| (12) | United States Patent | (10) Patent No.: | US 9,044,361 B2 |
|---|---|---|---|
| | Bell et al. | (45) Date of Patent: | Jun. 2, 2015 |

(54) PROXY CAREGIVER INTERFACE

(75) Inventors: Randall J. Bell, Hamilton, OH (US);
James M. Allen, Batesville, IN (US);
Dan R. Tallent, Hope, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 54 days.

(21) Appl. No.: 13/556,255

(22) Filed: Jul. 24, 2012

(65) Prior Publication Data

US 2014/0026322 A1    Jan. 30, 2014

(51) Int. Cl.
| *A61G 7/002* | (2006.01) |
| *G06F 19/00* | (2011.01) |
| *A61G 7/00* | (2006.01) |
| *A61G 7/018* | (2006.01) |
| *A61B 5/00* | (2006.01) |
| *A61G 7/015* | (2006.01) |
| *A61B 5/11* | (2006.01) |

(52) U.S. Cl.
CPC . *A61G 7/00* (2013.01); *A61G 7/018* (2013.01); *A61B 5/002* (2013.01); *A61G 7/015* (2013.01); *A61B 5/1113* (2013.01); *A61B 5/0022* (2013.01); *A61G 7/002* (2013.01); *G06F 19/3406* (2013.01); *A61G 2203/12* (2013.01); *A61G 2203/20* (2013.01)

(58) Field of Classification Search
CPC ......... A61G 7/00; A61G 7/018; A61G 7/015; A61G 7/002; A61G 2203/12; A61G 2203/20; A61B 5/002; A61B 5/1113; A61B 5/0022; G06F 19/3406
USPC ............................... 5/600, 613, 616; 715/738
See application file for complete search history.

(56) References Cited

U.S. PATENT DOCUMENTS

| 2,152,431 | A | 3/1939 | Jensen |
| 2,501,267 | A | 3/1950 | Erikson |
| 3,157,889 | A | 11/1964 | Chanko |
| 3,329,978 | A | 7/1967 | Porter et al. |
| 3,724,003 | A | 4/1973 | Ellwanger et al. |
| 3,967,328 | A | 7/1976 | Cox |
| 4,012,799 | A | 3/1977 | Rutherford |
| 4,127,906 | A | 12/1978 | Zur |
| 4,435,862 | A | 3/1984 | King et al. |
| 4,776,047 | A | 10/1988 | DiMatteo |
| 5,036,557 | A | 8/1991 | Fales |

(Continued)

FOREIGN PATENT DOCUMENTS

WO     WO 03081414  A1  *  10/2003

OTHER PUBLICATIONS

Extended European Search Report for 13 177 119.8 dated Nov. 12, 2013, 6 pages.

*Primary Examiner* — Peter M Cuomo
*Assistant Examiner* — Brittany Wilson
(74) *Attorney, Agent, or Firm* — Barnes & Thornburg LLP

(57) ABSTRACT

A patient support apparatus for use in a healthcare facility has associated therewith a graphical user interface (GUI) that is operable to display information pertaining to features of the patient support apparatus and to display information pertaining to features of other patient support apparatuses. Under some circumstances, the GUI may also be used to control functions of some of the other patient support apparatuses. A bed data server is communicatively coupled to the patient support apparatus and to the other patient support apparatuses to control information flow to the GUI from the other patient support apparatuses.

19 Claims, 4 Drawing Sheets

(56) References Cited

U.S. PATENT DOCUMENTS

| | | |
|---|---|---|
| 5,123,916 A | 6/1992 | Riddle et al. |
| 5,158,568 A | 10/1992 | Riddle et al. |
| 5,171,260 A | 12/1992 | McIlwain |
| 5,320,641 A | 6/1994 | Riddle et al. |
| 5,468,216 A | 11/1995 | Johnson et al. |
| 5,555,581 A | 9/1996 | Woods |
| 5,615,430 A | 4/1997 | Nambu et al. |
| 5,628,078 A | 5/1997 | Pennington et al. |
| 5,642,537 A | 7/1997 | Johnson |
| 5,701,620 A | 12/1997 | Montross |
| 5,754,997 A | 5/1998 | Lussi et al. |
| 5,926,002 A | 7/1999 | Cavanaugh et al. |
| 6,038,718 A | 3/2000 | Pennington et al. |
| 6,351,678 B1 | 2/2002 | Borders |
| 6,560,492 B2 | 5/2003 | Borders |
| 6,611,979 B2 | 9/2003 | Welling et al. |
| 6,658,680 B2 | 12/2003 | Osborne et al. |
| 6,691,346 B2 | 2/2004 | Osborne et al. |
| 6,957,461 B2 | 10/2005 | Osborne et al. |
| 7,296,312 B2 | 11/2007 | Menkedick et al. |
| 7,319,386 B2 | 1/2008 | Collins, Jr. et al. |
| 7,538,659 B2 | 5/2009 | Ulrich et al. |
| 7,868,740 B2 | 1/2011 | McNeely et al. |
| 8,031,057 B2 | 10/2011 | McNeely et al. |
| 2002/0111701 A1 | 8/2002 | Borders |
| 2002/0196141 A1 | 12/2002 | Boone |
| 2003/0115672 A1 | 6/2003 | Newkirk |
| 2007/0210917 A1 | 9/2007 | Collins, Jr. et al. |
| 2008/0120784 A1 | 5/2008 | Warner |
| 2008/0172789 A1* | 7/2008 | Elliot et al. .................... 5/616 |
| 2008/0183048 A1* | 7/2008 | Zhang ........................ 600/300 |
| 2008/0235872 A1 | 10/2008 | Newkirk et al. |
| 2009/0212925 A1 | 8/2009 | Schuman, Sr. et al. |
| 2009/0212926 A1 | 8/2009 | Du et al. |
| 2009/0217080 A1 | 8/2009 | Ferguson et al. |
| 2012/0089419 A1 | 4/2012 | Huster et al. |

\* cited by examiner

PROXY CAREGIVER INTERFACE

BACKGROUND

The present disclosure relates to patient support apparatuses such as hospital beds. More particularly, the present disclosure relates to patient support apparatuses having graphical user interfaces for viewing data and entering commands.

Hospital beds having graphical user interfaces (GUI's), which are sometimes referred to as graphical caregiver interfaces (GCI's) by those skilled in the art, are known. The GUI's of some hospital beds are able to receive user inputs for controlling bed functions and are able to display a wide variety of data or information to caregivers. Some of the types of bed information displayed on such GUI's may include, for example, bed height data, bed position data (e.g., horizontal, recumbent, fowler, cardiac, leg raised, vascular, Trendelenburg, reverse Trendelenburg, and chair), head angle, brake status data, side rail status data, surface state (e.g., normal, max-inflate, sleep mode, seat deflate, alternating pressure, wave mode such as Hill-Rom's OPTIREST™ feature, left/right turn assist, and continuous lateral rotation therapy). Some of the bed functions controllable with GUI's of hospital beds may include, for example, articulation of head, thigh, and foot sections, bed height adjustments, brake set/release, and surface control functions for those hospital beds having an integrated bed frame and mattress system.

GUI's of some hospital beds are also usable to control a weigh scale system and patient position monitoring (PPM) functions of beds. The GUI's of such beds typically display patient weight. Other patient information that may be displayed on a GUI of a hospital bed includes patient height, vital signs information (e.g., temperature, blood pressure, heart rate, respiration rate, and saturation of peripheral oxygen (SpO2)), inputs (e.g., fluids and solids) and outputs (e.g., fluids and solids). Various alarms are also displayed on GUI's of some prior art hospital beds. These alarms may include head angle alarms, PPM alarms, siderail position alarms, and so on.

Hospital bed manufacturers are known to offer GUI's as an option that can be purchased by healthcare facilities at an increased cost. Thus, beds that lack GUI's are usually less expensive than beds that have GUI's, assuming all other features of the beds with and without GUI's are equal. Of course, the beds without GUI's typically have manual-type user inputs such as buttons, knobs, levers, and the like for controlling various bed functions. Beds with GUI's oftentimes also include these manual-type user inputs, as well, for control redundancy. Accordingly, it will be appreciated that reducing the number of beds having GUI's represents a cost savings to healthcare facilities.

SUMMARY

An apparatus, system, or method may comprise one or more of the features recited in the appended claims and/or the following features which, alone or in any combination, may comprise patentable subject matter:

A patient support apparatus for use in a healthcare facility having at least one other patient support apparatus is provided. The patient support apparatus may include a patient support structure to support a patient, a graphical user interface (GUI), and control circuitry that may be carried by the patient support structure and that may be coupled to the GUI. The GUI may be operable to display information pertaining to features of the patient support apparatus and to display information pertaining to features of the at least one other patient support apparatus.

In some embodiments, the GUI may be operable to control functions of the patient support apparatus and to control functions of the at least one other patient support apparatus. According to this disclosure, the GUI may include a field that is selectable to obtain a menu of the at least one other patient support apparatus for which information may be obtained and/or that may be controlled using the GUI. The GUI may include visual indicia to indicate that the GUI is in a mode in which the data shown on the GUI pertains to one of the at least one other patient support apparatus and not the patient support apparatus and/or a mode in which the at least one other patient support apparatus is controllable with the GUI. For example, the visual indicia may include a colored border around a periphery of the GUI.

In some embodiments, if a first screen pertaining to the patient support apparatus is displayed on the GUI when the field is initially selected by a user to display the menu, then in response to one of the at least one other patient support apparatus being selected by the user from the menu, corresponding information to that of the first screen is shown on the GUI for the selected patient support apparatus.

According to this disclosure, the patient support apparatus comprises a first hospital bed and the at least one other patient support apparatus comprises a plurality of hospital beds. In some embodiments, the patient support structure may comprise a bed frame having a siderail that is moveable between a raised position to serve as a barrier inhibiting a patient from exiting the patient support structure and a lowered position permitting a patient to exit the patient support structure and the GUI may be mounted to the siderail. In other embodiments, the GUI is mounted to at least one of a wall and a piece of architectural equipment that is located in a room in which the patient support structure is located. Such architectural equipment may include, for example, a head wall unit, a bed locator unit, a column, a wall-mounted or ceiling-suspended arm, a cart, a service chase, and so forth.

According to an aspect of this disclosure, a system may include a first patient support apparatus that may have a graphical user interface (GUI) to view first data pertaining to the first patient support apparatus, a second patient support apparatus, and a bed data server remote from the first and second patient support apparatuses. The bed data server may be communicatively coupled to the first and second patient support apparatuses. The bed data server may provide second data pertaining to the second patient support apparatus to the first patient support apparatus for display on the GUI in response to user inputs entered on the GUI of the first patient support apparatus.

The GUI of the first patient support apparatus may include visual indicia, such as a colored border, to indicate that the GUI is displaying data pertaining to the second patient support apparatus. Alternatively or additionally, the visual indicia may include a room designator that indicates a location in a healthcare facility at which the second patient support apparatus is located.

According to some embodiments of this disclosure, if the first and second patient support apparatuses are located in a common room of a healthcare facility, then the GUI may be usable to control functions of both the first and second patient support apparatuses. However, if the first and second patient support apparatuses are located in different rooms of the healthcare facility, then the GUI is usable to control functions of the first patient support apparatus but not the second patient support apparatus. In either case, the GUI is operable to display the first data from the first patient support apparatus and the second data from the second patient support apparatus.

Additional patient support apparatuses may be communicatively coupled to the GUI of the first patient support apparatus via the bed data server. Accordingly, the system may further include a third patient support apparatus communicatively coupled to the bed data server. The bed data server, therefore, may provide third data pertaining to the third patient support apparatus to the first patient support apparatus for display on the GUI in response to user inputs entered on the GUI of the first patient support apparatus. The GUI may display a field that is selectable to obtain a menu that lists designators for the second and third patient support apparatuses for selection by a user. For example, the designators each may comprise a patient identifier and/or a room location identifier.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
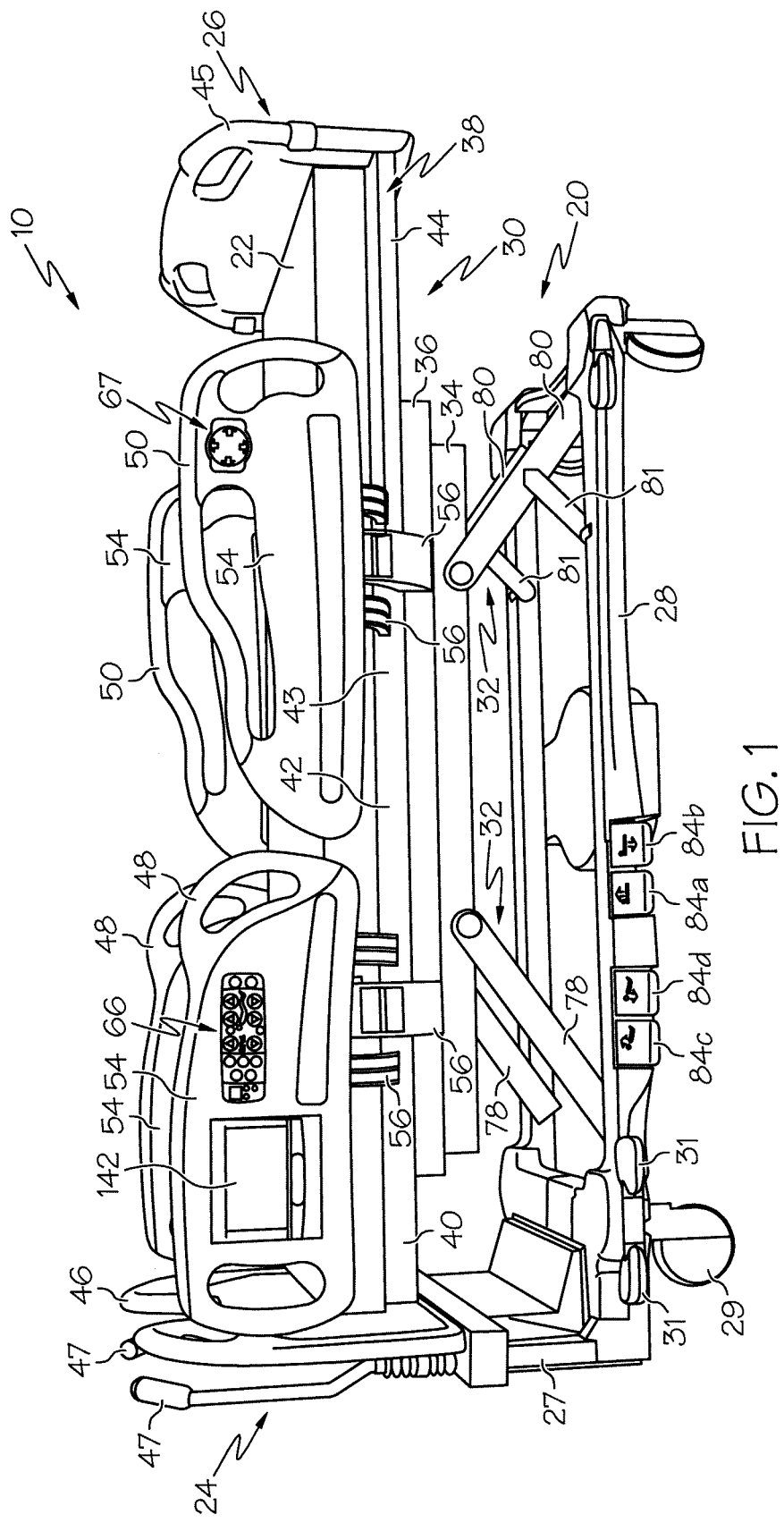
FIG. 1 is a perspective view of a hospital bed having a graphical user interface (GUI) or display screen coupled to a siderail of the hospital bed.

A patient support apparatus, such as illustrative hospital bed 10, includes a patient support structure such as a frame 20 that supports a surface or mattress 22 as shown in FIG. 1. Thus, according to this disclosure a bed frame, a mattress or both are examples of things considered to be within the scope of the term "patient support structure." However, this disclosure is applicable to other types of patient support apparatuses and other patient support structures, including other types of beds, surgical tables, examination tables, stretchers, and the like. As will be described below in further detail, a graphical user interface (GUI) 142 of bed 10 is operable to view data or information from other beds 10' and, in some circumstances of some contemplated embodiments, is operable to control features or functions of other beds 10'.

Referring again to FIG. 1, frame 20 of bed 10 includes a base 28, an upper frame assembly 30 and a lift system 32 coupling upper frame assembly 30 to base 28. Lift system 32 is operable to raise, lower, and tilt upper frame assembly 30 relative to base 28. Bed 10 has a head end 24 and a foot end 26. Hospital bed 10 further includes a footboard 45 at the foot end 26 and a headboard 46 at the head end 24. Illustrative bed 10 includes a pair of push handles 47 coupled to an upstanding portion 27 of base 28 at the head end 24 of bed 10. Headboard 46 is coupled to upstanding portion 27 of base 28 as well. Footboard 45 is coupled to upper frame assembly 30. Base 28 includes wheels or casters 29 that roll along a floor (not shown) as bed 10 is moved from one location to another. A set of foot pedals 31 are coupled to base 31 and are used to brake and release casters 29.

Illustrative hospital bed 10 has four siderail assemblies coupled to upper frame assembly 30 as shown in FIG. 1. The four siderail assemblies include a pair of head siderail assemblies 48 (sometimes referred to as head rails) and a pair of foot siderail assemblies 50 (sometimes referred to as foot rails). Each of the siderail assemblies 48, 50 is movable between a raised position, as shown in FIG. 1, and a lowered position (not shown but well-known to those skilled in the art). Siderail assemblies 48, 50 are sometimes referred to herein as siderails 48, 50. Each siderail 48, 50 includes a barrier panel 54 and a linkage 56. Each linkage 56 is coupled to the upper frame assembly 30 and is configured to guide the barrier panel 54 during movement of siderails 48, 50 between the respective raised and lowered positions. Barrier panel 54 is maintained by the linkage 56 in a substantially vertical orientation during movement of siderails 48, 50 between the respective raised and lowered positions.

Upper frame assembly 30 includes a lift frame 34, a weigh frame 36 supported with respect to lift frame 34, and a patient support deck 38. Patient support deck 38 is carried by weigh frame 36 and engages a bottom surface of mattress 22. Patient support deck 38 includes a head section 40, a seat section 42, a thigh section 43 and a foot section 44 in the illustrative example as shown in FIG. 1 and as shown diagrammatically in FIG. 2. Sections 40, 43, 44 are each movable relative to weigh frame 36. For example, head section 40 pivotably raises and lowers relative to seat section 42 whereas foot section 44 pivotably raises and lowers relative to thigh section 43. Additionally, thigh section 43 articulates relative to seat section 42. Also, in some embodiments, foot section 44 is extendable and retractable to change the overall length of foot section 44 and therefore, to change the overall length of deck 38. For example, foot section 44 includes a main portion 45 and an extension 47 in some embodiments as shown diagrammatically in FIG. 2.

In the illustrative embodiment, seat section 42 is fixed in position with respect to weigh frame 36 as patient support deck 38 moves between its various patient supporting positions including a horizontal position, shown in FIG. 1, to support the patient in a supine position, for example, and a chair position (not shown) to support the patient in a sitting up position. In other embodiments, seat section 42 also moves relative to weigh frame 36, such as by pivoting and/or translating. Of course, in those embodiments in which seat section 42 translates along upper frame 42, the thigh and foot sections 43, 44 also translate along with seat section 42. As bed 10 moves from the bed position to the chair position, foot section 44 lowers relative to thigh section 43 and shortens in length due to retraction of the extension 47 relative to main portion 45. As bed 10 moves from the chair position to the bed position, foot section 44 raises relative to thigh section 43 and increases in length due to extension of the extension relative to main portion 45. Thus, in the chair position, head section 40 extends upwardly from weigh frame 36 and foot section extends downwardly from thigh section 43.

Figure 2:
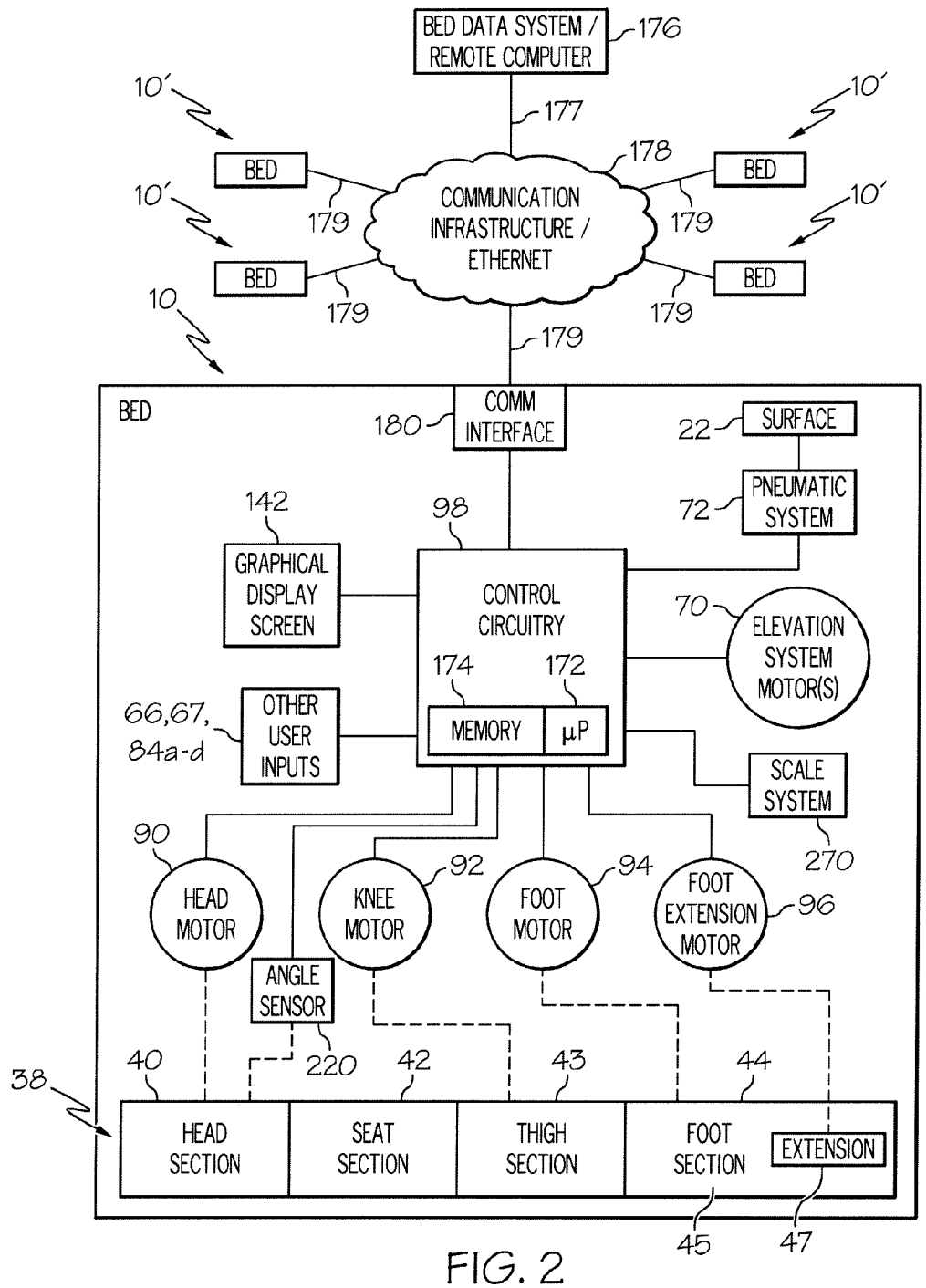
FIG. 2 is a block diagram showing electrical circuitry of the hospital bed in communication with a remote computer and other hospital beds also in communication with the remote computer.

As shown diagrammatically in FIG. 2, bed 10 includes a head motor or actuator 90 coupled to head section 40, a knee motor or actuator 92 coupled to thigh section 43, a foot motor or actuator 94 coupled to foot section 44, and a foot extension motor or actuator 96 coupled to foot extension 47. Motors 90, 92, 94, 96 may include, for example, an electric motor of a linear actuator. In those embodiments in which seat section 42 translates along upper frame 30 as mentioned above, a seat motor or actuator (not shown) is also provided. Head motor 90 is operable to raise and lower head section 40, knee motor 92 is operable to articulate thigh section 43 relative to seat section 42, foot motor 94 is operable to raise and lower foot section 44 relative to thigh section 43, and foot extension motor 96 is operable to extend and retract extension 47 of foot section 44 relative to main portion 44 of foot section 44.

In some embodiments, bed 10 includes a pneumatic system 72 that controls inflation and deflation of various air bladders or cells of mattress 22. The pneumatic system 72 is represented in FIG. 2 as a single block but that block 72 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses of hospital beds.

As also shown diagrammatically in FIG. 2, lift system 32 of bed 10 includes one or more elevation system motors or actuators 70, which in some embodiments, comprise linear actuators with electric motors. Thus, actuators 70 are sometimes referred to herein as motors 70. Alternative actuators or motors contemplated by this disclosure include hydraulic cylinders and pneumatic cylinders, for example. The motors 70 of lift system 32 are operable to raise, lower, and tilt upper frame assembly 30 relative to base 28. In the illustrative embodiment, one of motors 70 is coupled to, and acts upon, a set of head end lift arms 78 and another of motors 70 is coupled to, and acts upon, a set of foot end lift arms 80 to accomplish the raising, lowering and tilting functions of upper frame 30 relative to base 28. Guide links 81 are coupled to base 28 and to lift arms 80 in the illustrative example as shown in FIG. 1. Lift system of bed 10 is substantially similar to the lift system of the VERSACARE® bed available from Hill-Rom Company, Inc. Other aspects of bed 10 are also substantially similar to the VERSACARE® bed and are described in more detail in U.S. Pat. Nos. 6,658,680; 6,611,979; 6,691,346; 6,957,461; and 7,296,312, each of which is hereby expressly incorporated by reference herein.

In the illustrative example, bed 10 has four foot pedals 84a, 84b, 84c, 84d coupled to base 28 as shown in FIG. 1. Foot pedal 84a is used to raise upper frame assembly 30 relative to base 28, foot pedal 84b is used to lower frame assembly 30 relative to base 28, foot pedal 84c is used to raise head section 40 relative to frame 36, and foot pedal 84d is used to lower head section 40 relative to frame 36. In other embodiments, foot pedals 84a-d are omitted.

Each siderail 48 includes a first user control panel 66 coupled to the outward side of the associated barrier panel 54 and each siderail 50 includes a second user control panel 67 coupled to the outward side of the associated barrier panel 54.

Controls panels 66, 67 include various buttons that are used by a caregiver (not shown) to control associated functions of bed 10. For example, control panel 66 includes buttons that are used to operate head motor 90 to raise and lower the head section 40, buttons that are used to operate knee motor to raise and lower the thigh section, and buttons that are used to operate motors 70 to raise, lower, and tilt upper frame assembly 30 relative to base 28. In the illustrative embodiment, control panel 67 includes buttons that are used to operate motor 94 to raise and lower foot section 44 and buttons that are used to operate motor 96 to extend and retract foot extension 47 relative to main portion 45. In some embodiments, the buttons of control panels 66, 67 comprise membrane switches.

As shown diagrammatically in FIG. 2, bed 10 includes control circuitry 98 that is electrically coupled to motors 90, 92, 94, 96 and to motors 70 of lift system 32. Control circuitry 98 is represented diagrammatically as a single block 98 in FIG. 6, but control circuitry 98 in some embodiments comprises various circuit boards, electronics modules, and the like that are electrically and communicatively interconnected. Control circuitry 98 includes one or more microprocessors 172 or microcontrollers that execute software to perform the various bed control functions and algorithms described herein. Thus, circuitry 98 also includes memory 174 for storing software, variables, calculated values, and the like as is well known in the art.

As also shown diagrammatically in FIG. 2, a user inputs block represents the various user inputs such as buttons of control panels 66, 67 and pedals 84a-d, for example, that are used by the caregiver or patient to communicate input signals to control circuitry 98 of bed 10 to command the operation of the various motors 70, 90, 92, 94, 96 of bed 10, as well as commanding the operation of other functions of bed 10. Bed 10 includes at least one graphical user input (GUI) or display screen 142 coupled to a respective siderail 48 as shown in FIG. 1. Display screen 142 is coupled to control circuitry 98 as shown diagrammatically in FIG. 2. In some embodiments, two GUI's 142 are provided and are coupled to respective siderails 48. Alternatively or additionally, one or more GUI's are coupled to siderails 50 and/or to one or both of the headboard 46 and footboard 45. Thus, it is contemplated by this disclosure that a GUI 142 may be coupled to any of barriers 45, 46, 48, 50 of bed 10. Alternatively or additionally, GUI 142 is provided on a hand-held device such as a pod or pendant that communicates via a wired or wireless connection with control circuitry 98.

Control circuitry 98 receives user input commands, sometimes referred to herein as simply "user inputs," from GUI 142 when display screen 142 is activated. The user input commands control various functions of bed 10 such as controlling the pneumatic system 72 and therefore, the surface functions of surface 22. In other embodiments, surface 22 is not controlled by GUI 142. In some embodiments, the input commands entered on GUI 142 also control the functions of one or more of motors 70, 90, 92, 94, 96 but this need not be the case. In some embodiments, input commands entered on the user interface 142 also control functions of a scale system 270, which is discussed in more detail below. Various examples of the various alternative or additional functions of bed 10 that are controlled by GUI 142 in various embodiments can be found in U.S. Patent Application Publication Nos. 2012/0089419 A1, 2008/0235872 A1 and 2008/0172789 A1, each of which is hereby incorporated by reference herein to the extent that it is not inconsistent with the present disclosure which shall control as to any inconsistencies.

In some embodiments, control circuitry 98 of bed 10 communicates with a remote computer device 176 via communication infrastructure 178 such as an Ethernet of a healthcare facility in which bed 10 is located and via communications links 177, 179 as shown diagrammatically in FIG. 2. Infrastructure 178 may be operated according to, for example, the IEEE 802.3 (wired Ethernet) standard and/or the IEEE 802.11 (wireless Ethernet) standard. Computer device 176 is sometimes simply referred to as a "computer" or a "server" herein. Remote computer 176 may be part of a bed data system, for example. One example of a bed data system is shown and described in U.S. application Ser. No. 13/487,400 which was filed Jun. 4, 2012, which was titled "System and Method of Bed Data Aggregation, Normalization, and Communication to Third Parties," and which is hereby incorporated herein by reference to the extent that it is not inconsistent with the present disclosure which shall control as to any inconsistencies. Alternatively or additionally, it is within the scope of this disclosure for circuitry 98 of bed 10 to communicate with other computers such as those included as part of an electronic medical records (EMR) system, a nurse call system, a physician ordering system, an admission/discharge/transfer (ADT) system, or some other system used in a healthcare facility in other embodiments, although this need not be the case. Ethernet 178 in FIG. 2 is illustrated diagrammatically and is intended to represent all of the hardware and software that comprises a network of a healthcare facility.

In the illustrative embodiment, bed 10 has a communication interface or port 180 which provides bidirectional communication via link 179 with infrastructure 178 which, in turn, communicates bidirectionally with computer 176 via link 177. Link 179 is a wired communication link in some embodiments and is a wireless communications link in other embodiments. Thus, communications link 179, in some embodiments, comprises a cable that connects bed 10 to a wall mounted jack that is included as part of a bed interface unit (BIU) or a network interface unit (NIU) of the type shown and described in U.S. Pat. Nos. 7,538,659 and 7,319,386 and in U.S. Patent Application Publication Nos. 2009/0217080 A1, 2009/0212925 A1 and 2009/0212926 A1, each of which is hereby expressly incorporated by reference herein to the extent that it is not inconsistent with the present disclosure which shall control as to any inconsistencies. In other embodiments, communications link 179 comprises wireless signals sent between bed 10 and a wireless interface unit or a wireless access point of the type shown and described in U.S. Patent Application Publication No. 2007/0210917 A1 which is hereby expressly incorporated by reference herein to the extent that it is not inconsistent with the present disclosure which shall control as to any inconsistencies. Thus, communications link 177 comprises one or more wired links and/or wireless links as well, according to this disclosure.

As also shown diagrammatically in FIG. 2, a plurality of other hospital beds 10' are also coupled to communication infrastructure 178 via respective communications links 179, some or all of which may be wired links 179 and some or all of which may be wireless links 179. As mentioned previously, GUI 142 is operable to display data or information from other beds 10' and/or to control features or functions of other beds 10' in some instances. Accordingly, if any of beds 10' do not have a GUI, the bed 10 that does have GUI 142 may still be used to display information pertaining to the other beds 10'.

With regard to using GUI 142 of one bed 10 to control features or functions of other beds 10', in some embodiments a distinction is made between controlling active features or functions and passive features or functions of any particular bed 10'. Active features or functions are those in which one portion of bed 10' moves relative to another portion of bed 10'. Thus, deck articulation functions as well as raising, lowering, or tilting the upper frame relative to the base frame are examples of active functions or features. Accordingly, for active features, GUI 142 of one bed 10 is used to control, for example, one or more of motors 70, 90, 92, 94, 96 of another bed 10'. On the other hand, passive features or functions include, for example, controlling a PPM system of bed 10, 10' (e.g., enabling or disabling the PPM system, changing the mode of operation of the PPM system, changing the volume of a local alarm of the PPM system, etc.) or controlling a weigh scale system of bed 10, 10'. Thus, the passive features or functions are typically associated with nonmoving portions of bed 10, 10'.

According to one embodiment contemplated by this disclosure, only active features or functions of beds 10, 10' that are within a line of sight of a caregiver from a particular bed 10 are able to be controlled by GUI 142 of that particular bed 10. Such beds 10, 10' may, for example, be located in the same room of a healthcare facility. The GUI of the particular bed 10 is disabled or blocked from being able to control active features or functions of beds 10' that are not in the caregiver's line of sight (e.g., beds 10' located in other rooms). The remote computer 176, therefore, serves as an administration computer that is operated or programmed in a manner that determines the various beds 10' for which the active features or functions may be controlled by the particular GUI 142 of bed 10. This is a safety feature that prevents a caregiver from moving portions of any of beds 10' that cannot be seen by the caregiver when using GUI 142 of bed 10. With regard to passive features or functions, in some embodiments, any bed 10 having a GUI 142 may be used to control all of the passive features or functions of other beds 10' that are communicatively coupled together via infrastructure 178.

Figure 3:
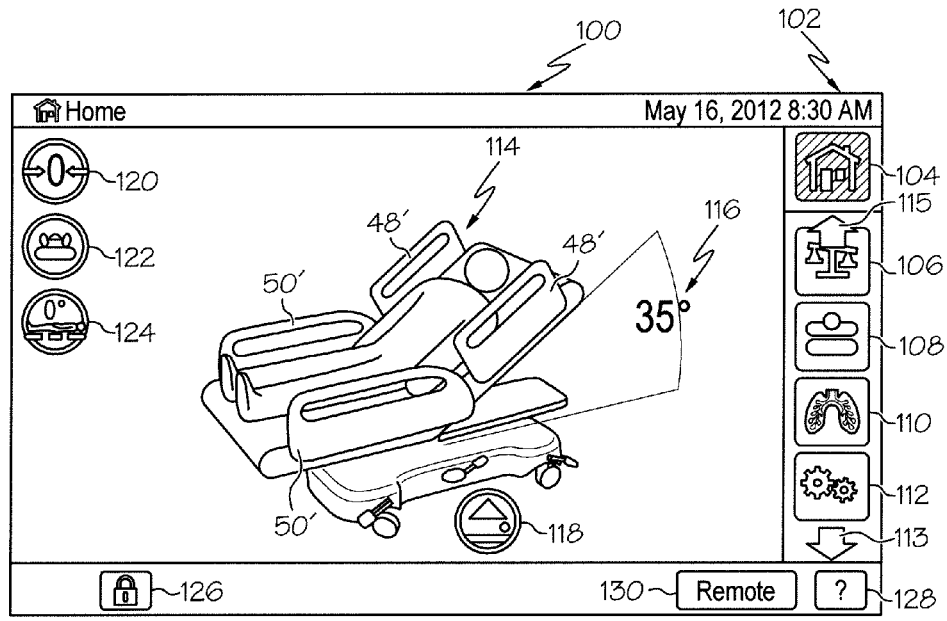
FIG. 3 is a screen shot showing a home screen having a column of main menu icons or buttons on the right hand side of the home screen and a Remote button or icon located generally beneath the main menu icons.

Referring now to FIG. 3, a home screen 100 of bed 10 that appears on GUI 142 in response to GUI 142 being awakened out of a non-interaction mode or screen saver mode includes a menu 102 of icons for navigating to other screens. With regard to awakening GUI 142 from the non-interaction mode, see U.S. application Ser. No. 13/360,846 which was filed Jan. 30, 2012, which is titled "Graphical Caregiver Interface with Swipe to Unlock Feature," and which is hereby expressly incorporated by reference herein to the extent that it is not inconsistent with the present disclosure which shall control as to any inconsistencies. Menu 102 includes a home icon (sometimes referred to herein as a "button") 104, a scale icon 106, a mattress set up icon 108, a therapy control icon 110, and a preference icon 112. Because home screen 100 is being shown on GUI 142, the corresponding home icon 104 is highlighted in FIG. 3, as indicated by the cross hatching on icon 104.

Icons 106, 108, 110, 112 are selectable by the user to navigate to one or more screens associated with those icons to gain access to bed data and to control features or functions of bed 10. For example, in some embodiments, selection of icon 106 results in a scale control screen being displayed on GUI 142 and that has one or more icons to permit the user to do one or more of the following: set a tare weight for the scale system, select whether pounds (lb) or kilograms (kg) are to be the units of measure for the patient's weight, enter data for use in calculation of the patient's BMI, or to take a weight reading. Selection of icon 108 results in a screen that permits the user to control surface operations such as, for example, maximum inflate, turn assist left, turn assist right and normal mode. Selection of icon 110 results in the user being able to navigate to screens to control therapy functions of mattress 22 such as, for example, continuous lateral rotation therapy, alternating pressure therapy, percussion and/or vibration therapy, and low air loss or microclimate management functions. Selection of icon 112 results in one or more screens that indicate the software version for the bed 10 and that permits the user to change the language setting, set the date and time, and set other GUI configuration parameters. Selection of icon 112 also provides access to bed maintenance features such as scale calibration, sensor calibration, and diagnostic trouble codes which involves reading and displaying failure codes from various electronics boards of beds 10, 10'.

A down arrow icon 113 appears at the bottom of menu 102 beneath icon 112 and is selected to scroll downwardly to reveal other icons (not shown) of menu 102. An up arrow icon 115 appears near the top of menu 102 just beneath the home icon 104 and is selected to scroll upwardly to reveal additional icons (not shown) of menu 102. Screen 100 also has a bed icon or indicia 114 that includes head angle data 116 as shown in FIG. 3. In the illustrative example, head angle data 116 indicates that the head section 40 of bed 10 has been raised by 35°. In some embodiment, the position of the siderails 48', 50' of bed icon 114 match the position of actual siderails 48, 50 of bed 10. Thus, if one of siderails 48, 50 is lowered, then icon 114 will show the corresponding siderail 48', 50' in a lowered position on home screen 100.

Screen 100 also has informational icons including a bed low icon 118 that appears beneath icon 114 and is green in color when the upper frame assembly 30 of bed 10 is in its lowermost position relative to base 28 and is yellow in color when the upper frame assembly 30 of bed 10 is not in its lowermost position relate to base 28. Another informational icon is a scale status icon 120 that indicates the scale status, whether the scale system 270 of bed 10 needs to be zeroed, or the date that the scale system 270 was zeroed. A further information icon is a surface status icon 122 that indicates the state of operation of the surface such as normal, maximum inflate, left turn assist, right turn assist, rotation left, rotation center, rotation right, percussion, vibration, OPTIREST™ mode (e.g., a mode in which zones of the mattress such as the head, seat thigh, and foot zones, are sequentially reduced in pressure one zone at a time to provide a wave effect for the patient), seat deflate, and sleep mode. The final informational icon is a Trend icon 124 that indicates whether the upper frame assembly 30 of bed 10 is in a flat or horizontal position, a Trendelenburg position, or a reverse Trendelenburg position.

Screen 100 further has a lock icon 126 that is selected to dim the GUI 142 and lock the GUI 142 from use in a non-interaction mode, a help icon 128 which is selected to obtain help on GUI 142 regarding the operation of bed 10, and a remote icon or button 130 which is selected to initiate the process of obtaining data and control icons on GUI 142 relating to other beds 10'. Icon 126 is selected, for example, when the caregiver intends to leave bed 10 and go elsewhere or when the caregiver intends to lean over the siderail 48 to which GUI 142 is coupled, so that inadvertent contact with GUI 142 will not result in inadvertent button selections.

Figure 4:
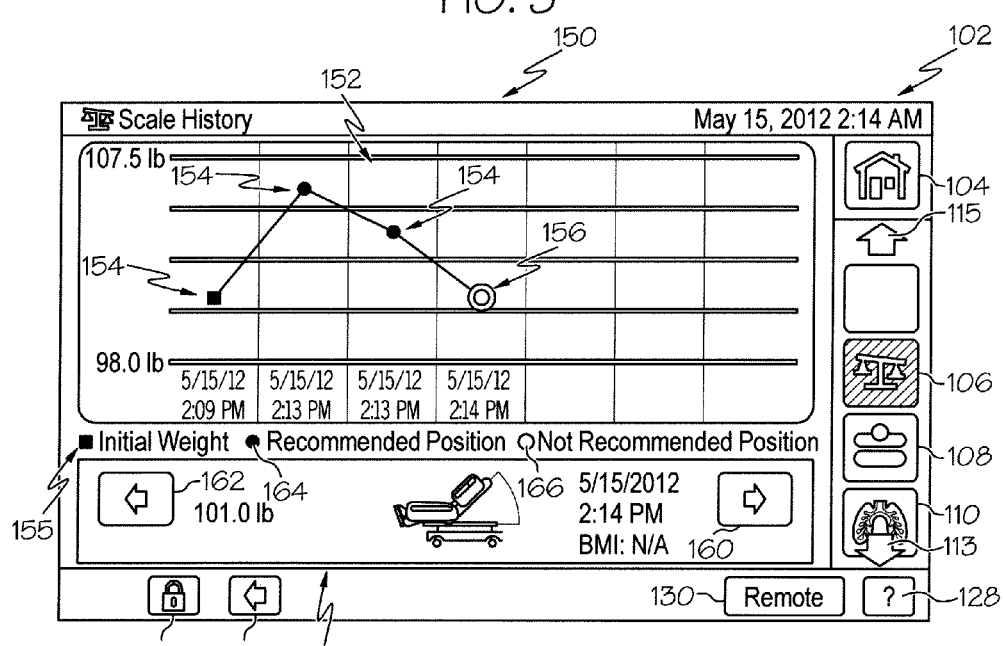
FIG. 4 is a screen shot showing a scale screen having graphical patient weight data associated with a first patient support apparatus.

Referring now to FIG. 4, a scale history screen 150 is shown. Screen 150 has many of the same icons as screen 100 and therefore, like reference numbers are used to denote the like icons and the descriptions of same are not repeated. Screen 150 has a scale history graph 152 with past data points 154 and a most recent data point 156. In the example of FIG. 4, an information bar 158 displays information about the most recent data point 156 including showing that the patient weight is 101.0 lb and was taken at 2:14 pm on May 15, 2012. In the illustrative example, body mass index (BMI) data is not available. A right arrow icon 160 and a left arrow icon 162 are situated at the opposite ends of information bar 158 and are used to scroll to other data points of the weight history graph 152.

The patient's initial weight is indicated on graph 152 with a solid square as explained by line of text 155 appearing on screen 150 beneath graph 152, and the past data points 154 are indicated with a solid dot or circle. The most recent data point 156 is indicated on graph 152 with a "bull's eye" image in the illustrative example because that is the data point having its associated information shown in bar 158. Accordingly, if left arrow icon 160 were to be selected, then the data point 154 just to the left of the most recent data point 156 would change to the "bull's eye" image and the most recent data point 156 would become a solid dot.

Screen 150 also has a Recommended Position radio button 164 and a Not Recommended Position radio button 166 beneath graph 152 as also shown in FIG. 4. For each data point 154, 156 having information shown in bar 158, one or the other of radio buttons 164, 166 is filled in to indicate whether the bed was (radio button 164) or was not (radio button 166) in a recommended position when the patient weight associated with the data point 154, 156 was taken. In the illustrative example, radio button 164 is filled in to indicate that bed 10 was in a recommended position when the weight of the patient associated with the most recent data point 156 was taken.

Screen 150 also has a back button or icon 168 that is selected when the user wishes to return to a previous screen (not shown) associated with the weigh scale system. The previous screen may be, for example, a screen used to do one or more of the following: set a tare weight for the scale system, select whether pounds (lb) or kilograms (kg) are to be the units of measure for the patient's weight, enter data for use in calculation of the patient's BMI, or to take a weight reading. Examples of screens having these sorts of weigh scale system functions are included in various ones of the documents already incorporated herein by reference.

Figure 5:
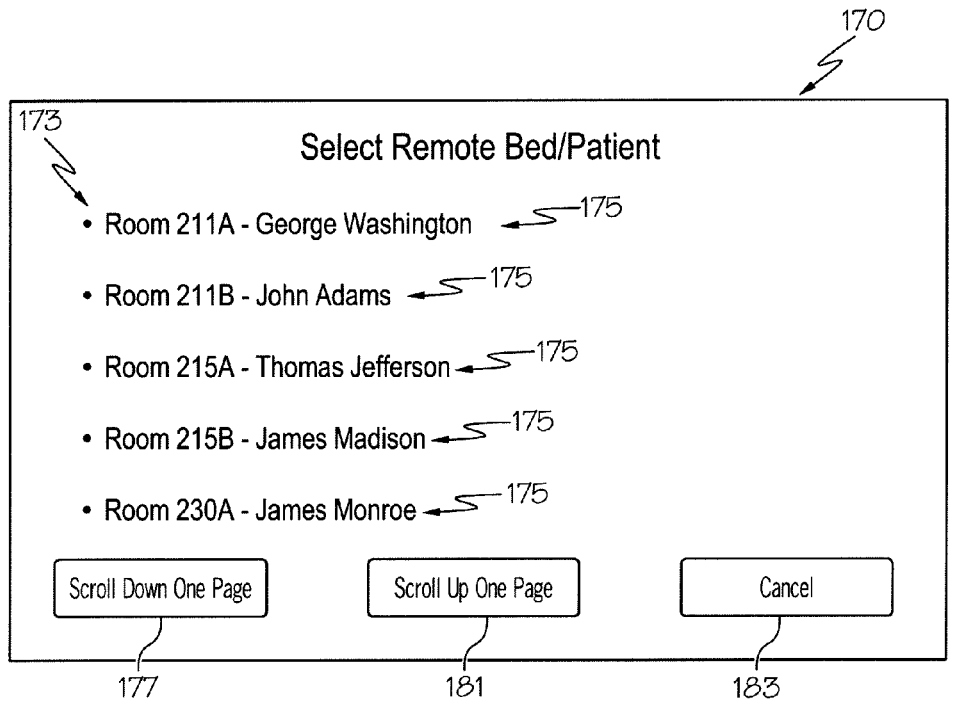
FIG. 5 is a screen shot showing a Remote Bed/Patient menu screen that is displayed on the GUI in response to the Remote button or field being selected, the Remote Bed/Patient menu screen having a menu listing other patient support apparatuses for which patient data and bed control icons may be displayed.

Referring now to FIG. 5, a Remote Bed/Patient menu screen 170 appears on GUI 142 in response to the user selecting the remote icon 130 at any time on any of the various screens that appear on GUI 142 having icon 130, such as home screen 100 of FIG. 3 or scale history screen 150 of FIG. 4. Screen 170 has a list 173 of the room numbers and/or patient names that define fields or areas 175 on screen 170 that can be selected to obtain data or information pertaining to the bed 10' associated with the room or patient of the selected field 175 and/or to control features and functions of the bed 10' associated with the room or patient of the selected field 175.

Screen 170 also has a Scroll Down One Page button or icon 177, a Scroll Up One Page button or icon 181, and a Cancel button or icon 183 as shown in FIG. 5. Buttons 177, 181 are selected to scroll down or up, as the case may be, the list 173 to reveal additional room numbers and/or patient names for which information and/or controls of additional beds 10' can be selected for display on GUI 142 of bed 10. Button 183 is selected if the user wishes to return to the previous screen on which the user had previously selected the Remote button 130.

Figure 6:
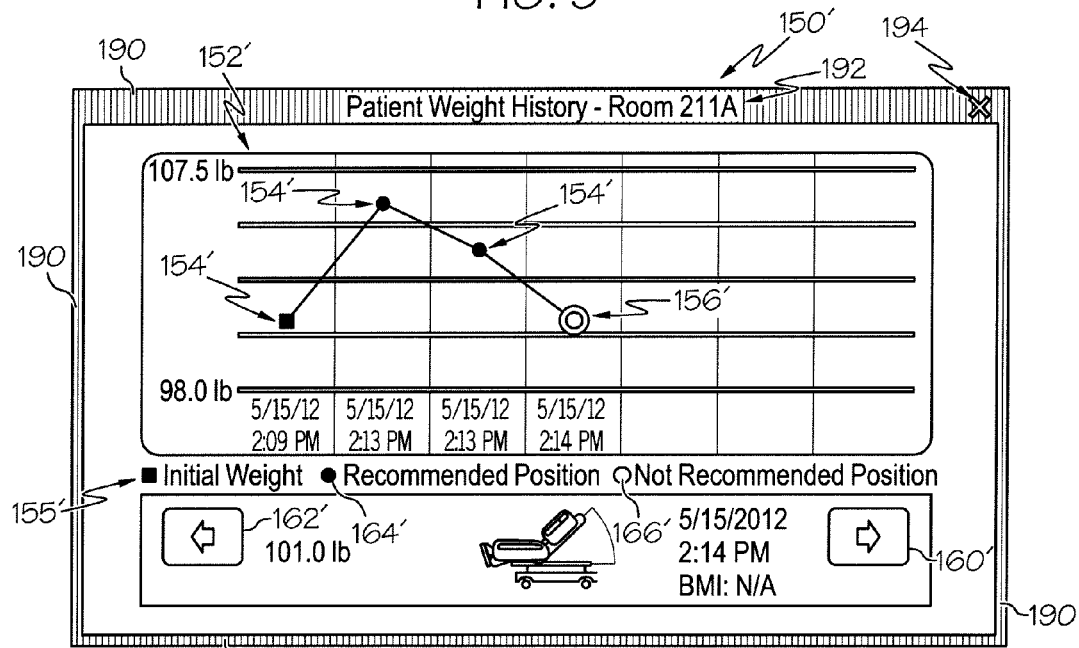
FIG. 6 is a screen shot of a Remote scale screen having graphical weight data associated with a second patient support apparatus being displayed on the GUI of the first patient support apparatus and showing a colored border providing a visual indicia to indicate that the data being displayed is not associated with the first patient support apparatus.

In response to the user selecting one of fields 175, the resulting graphics that appear on GUI 142 of bed 10 are those pertaining to the bed 10' associated with the selected field 175 and correspond to the same graphics that were previously shown on screen 142 at the time the user initially selected remote button 130. To illustrate this point, assuming that the user was viewing screen 150 of FIG. 4 at the time of selecting button 130 and assuming the user selected the first field 175 shown in list 173 of screen 170 of FIG. 5 (i.e., the field indicating "Room 211A—George Washington"), then a proxy screen 150' appears on GUI 142 of bed 10 with a patient weight history graph 152' having past weight data points 154' and a most recent weight data point 156' for the patient on the bed 10' associated with the room of the selected field 174 as shown in FIG. 6. The other icons 155', 160', 162', 164', 166' appearing on proxy screen 150' represent the same information, data, feature or function, as the case may be, as icons 155, 160, 162, 164, 166 of screen 150 discussed above, except of course, they pertain to bed 10' and not bed 10.

In order to visually indicate to the user that the graphics displayed on GUI 142 pertains to one of beds 10' and not bed 10, a colored border 190 appears around the periphery of the display screen of GUI 142 as shown in FIG. 6. In one embodiment, the colored border is pink, which is indicated in FIG. 6 using vertical cross hatching. However, it is within the scope of this disclosure for any suitable color to be used for border 190 although, it will be appreciated that it is beneficial if the color used for border 190 is in stark contrast to other colors appearing on the screen and particularly, in stark contrast to the background color of the screen. Screen 150' in the illustrative example also has a line of text 192 in the top portion of border 190 that indicates the room number of the bed 10' to which the displayed graphics pertain. A close icon 194 appears in the upper right hand corner of screen 150' within border 190 and is selected when the user no longer wishes to view data or have control over bed 10'.

In the illustrative example, screen 150' does not have any icons or buttons that would permit the user to navigate to other screens having information and controls of other types for bed 10'. Specifically, screen 150' does not have any icons corresponding to icons 104, 106, 108, 110, 113, 115, 168 of screen 150. Thus, to get to another screen of bed 10', the user closes screen 150' using close icon 194 then navigates to another screen pertaining to bed 10, then selects the remote icon 130 of that screen and the particular field 175 on screen 170 associated with bed 10' to see the new screen pertaining to bed 10'. In other embodiments, screen 150' has icons like icons 104, 106, 108, 110, 113, 115, 168 of screen 150 that permits the user to navigate from screen to screen pertaining to bed 10'. In such embodiments, border 190 remains displayed on GUI 142 so the user is constantly reminded that the screens being viewed pertains to one of beds 10' and not bed 10.

While weight history screens 150, 150' of beds 10, 10', respectively, are used in the present disclosure to illustrate the basic concept of how GUI 142 of bed 10 is used as a proxy for information and/or controls of any of beds 10' networked to bed 10 via infrastructure 178 and communications links 179, it will be appreciated that it is within the scope of this disclosure for many other screen types having all sorts of bed data and bed functionality pertaining to bed 10' to be displayed on GUI 142 of bed 10 in a similar manner. Accordingly, it is contemplated by this disclosure that any and all of the screens shown in the various references already incorporated by reference herein, and particularly those shown in U.S. Patent Application Publication Nos. 2012/0089419 A1, 2008/0235872 A1 and 2008/0172789 A1, could be modified to have a remote button or icon 130 that cooperates with control circuitry 98 of bed 10 in the same manner and achieve the same results as described herein with regard to the representative example of FIGS. 3-6.

In response to the user selecting remote icon 130, control circuitry 98 stores in memory 174 the screen type that was being displayed on GUI 142 at that time, which screen type correlates to a set of particular graphical elements representing bed functions and data that appear on that particular screen type. In response to the user thereafter selecting one of fields 175 on screen 170, control circuitry 98 then sends a message or query to remote computer or server 176 requesting the set of needed data and any other needed information pertaining to the bed 10' associated with the selected field 175. Computer 176 responds with the requested data and information which is stored in memory 174 for use in creating the proxy screen on bed 10 pertaining to bed 10'.

In response to user inputs being selected on GUI 142 of bed 10 to control bed 10', control messages are transmitted from control circuitry 98 of bed 10 to the appropriate bed 10' via interface 180, communication infrastructure 178, and communications links 179. The control messages sent from bed 10 to the appropriate bed 10' are also communicated to remote computer 176 in some embodiments, but this need not be the case. Acknowledgement messages are transmitted from bed 10' to bed 10 after receiving a control message in some embodiments.

It is contemplated by this disclosure that, when GUI 142 is being used as a proxy to display graphics pertaining to bed 10', various alarms that occur on bed 10' are shown on GUI 142 of bed 10. Thus, in some embodiments, an alarm message that is sent from bed 10' to remote computer 176 is, in turn, forwarded to bed 10 by computer 176. To accomplish that, computer 176 stores in its memory information regarding which bed 10' is having its information viewed on GUI 142 of bed 10. Alternatively, alarm messages from bed 10' are transmitted to bed 10 without involving remote computer 176. In such embodiments, bed 10' stores in its memory information regarding which bed 10 is being used as a proxy to view information pertaining to the particular bed 10' and then any alarm messages are addressed to bed 10. Acknowledgement of alarm messages by bed 10 to bed 10' and/or remote computer 176 is contemplated by this disclosure.

While GUI 142 is mounted directly to bed 10 in the illustrative example, a logical extension of the present disclosure is to mount GUI 142 to a wall or other structure that is near bed 10 but that is not otherwise part of bed 10. For example, GUI 142 is mounted to an architectural structure such as a headwall unit, bed locator unit, wall-supported arm, ceiling-supported arm, service chase, column, and so forth, in some embodiments. Such a wall-mounted or structure-mounted GUI 142 then communicates with control circuitry 98 of bed 10 via a suitable communication interface or port, such as one that is similar to interface 180, for example. Thus, according to this disclosure the wall-mounted or structure-mounted GUI 142 communicates with control circuitry 98 of bed 10 via a wired or wireless communication link. In such embodiments, GUI 142 operates in the same manner as described above to obtain data pertaining to other beds 10' and to control features or functions of other beds 10'.

Although certain illustrative embodiments have been described in detail above, many embodiments, variations and modifications are possible that are still within the scope and spirit of this disclosure as described herein and as defined in the following claims.

The invention claimed is:

1. A patient support apparatus for use in a healthcare facility having at least one other patient support apparatus, the patient support apparatus comprising
   a patient support structure to support a patient,
   a graphical user interface (GUI) mounted to the patient support structure, and
   control circuitry carried by the patient support structure and coupled to the graphical user interface, the graphical user interface being operable to display information pertaining to features of the patient support apparatus and to display information pertaining to features of the at least one other patient support apparatus, the patient support apparatus and the GUI being situated in a first room of a healthcare facility and the at least one other patient support apparatus being situated in a second room of the healthcare facility, wherein the GUI is operable to control functions of the patient support apparatus and to control functions of the at least one other patient support apparatus, wherein the patient support apparatus comprises at least one of a hospital bed, a surgical table, an examination table, or a stretcher and wherein the at least one other patient support apparatus comprises at least one of a hospital bed, a surgical table, an examination table, or a stretcher.

2. The patient support apparatus of claim 1, wherein the GUI includes visual indicia to indicate that the GUI is in a mode in which the at least one other patient support apparatus is controllable with the GUI.

3. The patient support apparatus of claim 2, wherein the visual indicia comprises a colored border around a periphery of the GUI.

4. The patient support apparatus of claim 1, wherein during use of the GUI to control functions of the patient support apparatus, the GUI includes a field that is selectable to obtain a menu of the at least one other patient support apparatus that may be controlled using the GUI.

5. The patient support apparatus of claim 1, wherein the GUI includes visual indicia to indicate that the GUI is in a mode in which the data shown on the GUI pertains to one of the at least one other patient support apparatus and not the patient support apparatus.

6. The patient support apparatus of claim 5, wherein the visual indicia comprises a colored border around a periphery of the GUI.

7. The patient support apparatus of claim 1, wherein during use of the GUI to display information pertaining to the patient support apparatus, the GUI includes a field that is selectable to obtain a menu of the at least one other patient support apparatus that may have associated information displayed on the GUI.

8. The patient support apparatus of claim 7, wherein if a first screen pertaining to the patient support apparatus is displayed on the GUI when the field is initially selected by a user to display the menu, then in response to one of the at least one other patient support apparatus being selected by the user from the menu, corresponding information to that of the first screen is shown on the GUI for the selected patient support apparatus.

9. The patient support apparatus of claim 1, wherein the patient support apparatus comprises a first hospital bed and the at least one other patient support apparatus comprises a plurality of hospital beds.

10. The patient support apparatus of claim 1, wherein the patient support structure comprises a bed frame having a siderail that is moveable between a raised position to serve as a barrier inhibiting a patient from exiting the patient support structure and a lowered position permitting a patient to exit the patient support structure and the GUI is mounted to the siderail.

11. The patient support apparatus of claim 1, wherein the GUI is mounted to at least one of a wall and a piece of architectural equipment that is located in a room in which the patient support structure is located.

12. A system comprising
a first patient support apparatus having mounted thereon a graphical user interface (GUI) to view first data pertaining to the first patient support apparatus,
a second patient support apparatus, the first patient support apparatus and the GUI being situated in a first room of a healthcare facility and the second patient support apparatus being situated in a second room of the healthcare facility, wherein the GUI is operable to control functions of the first patient support apparatus and to control functions of the second patient support apparatus, wherein the first patient support apparatus comprises at least one of a hospital bed, a surgical table, an examination table, or a stretcher and wherein the second patient support apparatus comprises at least one of a hospital bed, a surgical table, an examination table, or a stretcher, and
a bed data server remote from the first and second patient support apparatuses and communicatively coupled to the first and second patient support apparatuses, the bed data server providing second data pertaining to the second patient support apparatus to the first patient support apparatus for display on the GUI in response to user inputs entered on the GUI of the first patient support apparatus.

13. The system of claim 12, wherein the GUI of the first patient support apparatus includes visual indicia to indicate that the GUI is displaying data pertaining to the second patient support apparatus.

14. The system of claim 13, wherein the visual indicia comprises a colored border around a periphery of the GUI.

15. The system of claim 13, wherein the visual indicia includes a room designator that indicates a location in a healthcare facility at which the second patient support apparatus is located.

16. The system of claim 12, wherein the GUI is usable to control functions of the first patient support apparatus but not the second patient support apparatus.

17. The system of claim 12, further comprising a third patient support apparatus communicatively coupled to the bed data server, the bed data server providing third data pertaining to the third patient support apparatus to the first patient support apparatus for display on the GUI in response to user inputs entered on the GUI of the first patient support apparatus.

18. The system of claim 17, wherein the GUI displays a field that is selectable to obtain a menu that lists designators for the second and third patient support apparatuses for selection by a user.

19. The system of claim 18, wherein the designators each comprise at least one of a patient identifier and a room location identifier.

* * * * *